United States Patent [19]

Garsky

[11] 4,278,596
[45] Jul. 14, 1981

[54] ANALGESIC PENTAPEPTIDES

[75] Inventor: Victor M. Garsky, Radnor, Pa.

[73] Assignee: American Home Products Corporation, New York, N.Y.

[21] Appl. No.: 932,089

[22] Filed: Aug. 8, 1978

[51] Int. Cl.$^3$ .................. C07C 103/52; A61K 37/00
[52] U.S. Cl. .............................. 260/112.5 R; 424/177
[58] Field of Search .................. 424/177; 260/112.5 R

[56] References Cited

U.S. PATENT DOCUMENTS 4,128,541  12/1978  Sarantakis ........................... 424/177

FOREIGN PATENT DOCUMENTS 853448  10/1977  Belgium ............................. 260/112.5 R
2338925  8/1977  France ............................... 260/112.5 R

OTHER PUBLICATIONS

Coy et al., Biochem. and Biophys. Res. Commun. 73, 1976 632–637.
Life Science 21, (1977), 559–562.
British Journal of Pharmacology 59, 1977, pp. 455, 456.
Science 194, 330–332, 1976.
Opiates and Endogenous Opioid Peptides, 1976, 239–246; 87–94; 79–86.
Nature 262, 1976, 738–739.
Nature 258, 1975, 577–579.
Reprinted from Nature 260, No. 5552, pp. 625–626, 1976.

Primary Examiner—Delbert R. Phillips
Attorney, Agent, or Firm—Robert Wiser

[57] ABSTRACT

Pentapeptides of the formula:

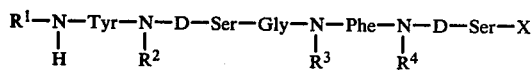

wherein $R^1$ is hydrogen, methyl, ethyl, propyl, 2-methyl-2-pentenyl, 2-methyl-1-pentenyl, cyclopropylmethyl, or cyclobutylmethyl; $R^2$, $R^3$, and $R^4$ are, independently, hydrogen or methyl; and X is —OH, —NH$_2$, —NHC$_n$H$_{2n+1}$ where n is 1, 2, 3, or 4, —OR$^3$, or CH$_2$OR$^3$, where $R^3$ is hydrogen or lower alkyl of from 1 to 4 carbon atoms; or a pharmaceutically acceptable salt thereof; have analgesic activity upon administration to warm-blooded animals.

5 Claims, No Drawings

ANALGESIC PENTAPEPTIDES

Enkephalin, a natural opiate receptor agonist in the brain, has been identified [see Hughes et al., Nature, 258, 577 (1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferns and guinea pig ileum, and both inhibit the stereospecific receptor binding of the opiate antagonist 3H-naloxone in brain homogenates.

It has been proposed that enkephalin receptors may be sites at which morphine-line drugs exert their analgesic activities, and that enkephalin may be the modulator or transmittor in brain systems for pain suppression or analgesia. It has been reported that methionine-enkephaline and leucine-enkephalin, when administered by injection in the brain ventricle in rats, induce a profound analgesia that is fully reversible by naloxone. [See Belluzzi et al., Nature, 260, 625 (1976)]. The enkephalins are inactive when administered peripherally, however, and it is believed that the enkephalins are rapidly destoryed by blood enzymes and/or are poorly transported across the blood-brain barrier.

The amino acid sequence of methionine-nekephalin is identical to that of the N-terminal portion of the C-fragment ($\beta$-endorphin or $\alpha$-LPH[61-91]) of the peptide $\beta$-lipotropin, which is found in large concentrations in the pituitary and in much lower concentrations in the brain. Other naturally-occurring fragments of $\beta$-lipotropin are known, for example: $\alpha$-endorphin ($\beta$LPH[61-76]) and $\gamma$-endorphin ($\beta$-LPH[61-77]). Both $\beta$-lipotropin and the endorphins show morphine-like properties in various test systems, and it has been suggested that methionine-enkephalin is a breakdown product of the large opiate-like peptides. Enkephalin, its relationship to $\beta$-lipotropin and the endorphins, and the pharmacological properties thereof, are reviewed in an article by Iverson et al., Nature, 262, 738 (1976). Recent developments are also described in detail in the "Proceedings of the International Narcotics Research Club Meeting", Aberdeen, U. K., July 19–22, 1976, published in *Opiates and Endorgenous Opioid Peptides*, North Holland Publishing Company, Amsterdam, 1976.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Change et al., Life Sciences, 18, 1473 (1976). Similarly, a long-acting synthetic pentapeptide, Tyr-D-Ala-Gly-Phe-Met-amide is described in Pert et al., Science, 194, 330 (1976); which compound, like the natural enkephalins, is inactive when administered peripherally. Baxter et al., British Journal of Pharmacology, Mar. 2, 1977, pages 445P–456P and 523P report activity in the compound Tyr-D-Ala-Gly-Phe-D-Leu when administered intracerebroventricularly.

SUMMARY OF THE INVENTION

The invention sought to be patented resides in the concept of a chemical compound of the formula:

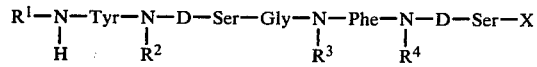

wherein $R^1$ is hydrogen, methyl, ethyl, propyl, 2-methyl-2-pentenyl, 2-methyl-1-pentenyl, cyclopropylmethyl, or cyclobutylmethyl; $R^2$, $R^3$, and $R^4$ are, independently, hydrogen or methyl; and X is $-NH_2$, $-NHC_nH_{2n+1}$ where n is 1, 2, 3, or 4, $-OR^5$, or $CH_2OR^5$, where $R^5$ is hydrogen or lower alkyl of from 1 to 4 carbon atoms; or a pharmaceutically acceptable salt thereof.

All chiral amino acids in the above formula, and throughout this specification and claims, are in the L- or natural configuration, unless otherwise indicated.

The tangible embodiments of the invention possess the inherent physical properties of being white to light tan colored solids, are substantially insoluble in organic solvents such as chloroform, benzene, and the like, but exhibit solubility in water and aqueous acid solutions such as hydrochloric and acetic. These compositions display no clearly discernable melting points. Amino acid analyses of the compositions of the invention are consistent with the structures as set forth.

The tangible embodiments of the invention possess the inherent applied use characteristics of producing analgesia upon administration to warm-blooded animals, as evidenced by standard test procedures.

Particularly preferred are compounds of the formula:

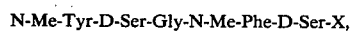

where X is $NH_2$ or $NHC_nH_{2n+1}$ where n is 1, 2, 3, or 4, or a pharmaceutically acceptable salt thereof.

DETAILED SPECIFICATION

The analgesic polypeptides of this invention are prepared by typical solid phase procedures employing either a benzhydrylamine polystyrene based resin for the production of the C-terminal amides or a chloromethylated or hydroxy methylated divinyl benzene cross-linked polystyrene resin for production of the C-terminal carboxylic acid or lower alkylamides. The polypeptide is removed from the resin support with HF and purified by gel filtration. These procedures are well-known in the art.

The pharmaceutically acceptable salts of the polypeptides of this invention are acid addition salts of the free base in which the acid may be either organic or inorganic, as for example, hydrochloric, phosphoric, maleic, acetic, citric, succinic, malic, and similar acids. Likewise, salts of the free peptidic acid are embraced by the expression "pharmaceutically acceptable salts", and include the sodium, potassium, ammonium, and lower alkylamine salts. The salts are prepared and isolated by conventional methods.

The analgesic activity of the polypeptides of this invention may be demonstrated by the rat-tail flick method of D'Amour and Smith, J. Pharmacol. Exp. Ther., 72, 74 (1941). In this procedure, a representative polypeptide of this invention, N-Me-Tyr-D-Ser-Gly-N-Me-Phe-D-Ser-NH$_2$, acetate, produced significant analgesia in rats upon administration at a dose as low as 0.1 mg/kg. intravenously, and 0.5 mg/kg. subcutaneously.

In employing the compounds of the invention, the particular dose to be administered will vary somewhat depending on the degree of analgesia desired, the particular animal being treated, and the particular compound of the invention being employed. In general, an intravenous dose of from 0.05 to 2.5 mg/kg. or a subcutaneous dose of from 0.5 to 10 mg/kg. will produce the desired effect. Preferably, analgesic therapy is initiated by administering a low dose of compound, the dosage thereafter being increased in succeeding administrations until the desired degree of analgesia is obtained. The precise dose for production of a desired effect will be readily determined by one skilled in the art.

The following examples for purpose of illustration, describe in detail the synthesis of particular compounds of the invention. The other compounds of the invention may be made in similar fashion by substituting the desired blocked amino acid at the appropriate step of the process.

EXAMPLE 1

N-Methyl-Tyrosyl-D-Serylglycyl-N-MethylPhenylalanyl-D-Serinamide. Acetate

To a 200 ml. reaction vessel was added 10.0 g. of benzhydrylamine resin (9 m moles free amine content). The resin was then treated in the following manner:
1. methylene chloride (three times).
2. 5 minute prewash with 30% trifluoroacetic acid-methylene chloride (v/v) containing 0.5% dithioerythritol.
3. 25 minute treatment with the above-described trifluoroacetic acid.
4. methylene chloride (three times).
5. 10 minute treatment with triethylamine-dimethylformamide (v/v).
6. dimethylformamide (three times).
7. methylene chloride (three times).

A contact time of 2 minutes was allowed for each wash unless otherwise indicated.

The resin was gently stirred with t-Boc-O-Bzl-D-Ser and 1-hydroxybenzotriazole (HOBT) in 50% methylene chloride-dimethylformamide (20 m moles t-Boc-O-Bzl-D-Ser and 22 m moles HOBT). Following the addition of the above reagents, the mixture was treated with 22 mm. of diisopropylcarbodiimide (the DIC was added in two equal portions over 30 minutes). After stirring overnight, the peptide-resin was washed successively with dimethylformamide (twice), 12% triethylamine-dimethylformamide (once) and methylene chloride (thrice). To test for completeness of reaction, the peptide-resin was subjected to a ninhydrin color test following the procedure of E Kaiser et al., Analytical Chemistry, 34, 595 (1970).

The deprotection of the attached amino acid was carried out as described in steps (2) through (7) above.

The following amino acid residues were then introduced consecutively: t-Boc-N-Me-Phe (20 m moles, 22 m moles HOBT and 22 m moles DIC), t-Boc-glycine (20 m moles, 22 m moles HOBT and 22 m moles DIC), t-Boc-O-Bzl-D-Ser (20 m moles, 22 m moles HOBT and 22 m moles DIC), t-Boc-N-Me-O-2,6-Cl-Bzl-Tyr (20 m moles, 22 m moles HOBT and 22 m moles DIC). The washed pentapeptide resin was dried in vacuo to yield 13.4 g.

The above-described pentapeptide resin (13.4 g) was treated in vacuo with anhydrous liquid hydrogen fluoride (100 ml.) and anisole (10 ml.) at 0° for 1 hour. The hydrogen fluoride and anisole were removed under reduced pressure and the residue suspended in 2N acetic acid, filtered and the filtrate lyophilized to yield the above title product, 2.91 g.

The crude product was treated with AG-3-X4A ion exchange resin (acetate form) for 30 min., filtered and lyophilized, 2.65 g.

EXAMPLE 2

Purification and Characterization of N-Methyl-Tyrosyl-D-Serylglycyl-N-Methyl-Phenylalanyl-D-Serinamide. Acetate The above-titled crude product was purified as follows: 1.3 g of material is dissolved in a minimum amount of 2N acetic acid and applied to a column (2.5×200 cm.) of Sephadex G-10 in 2N acetic acid. The column was eluted with 2N acetic acid and 15 ml. fractions collected. The column effluent was monitored at 254 nm. Fractions 29–40 were combined and lyophilized to yield 0.979 g. The product (0.979 g.) was further purified by applying the material in a small volume of upper phase B:A:W, 4:1:5 (n-butanol:acetic acid:water) onto a column (2.5×150 cm.) of Sephadex G-25 medium previously equilibrated with lower phase of the above system and then upper phase. The column was eluted with upper phase B:A:W and 11 ml. fractions collected. The effluent was monitored as above. Tubes 79–90 were shown to be homogeneous by thin layer chromatography systems 4:1:5; $R_f$=0.28 and 7:7:6 (isoamyl alcohol:pyridine:water); $R_f$=0.66 on silica gel. Thin layer chromatograms were visualized with ninhydrin and chlorine peptide reagent. Amino acid analysis following methane sulfonic acid hydrolysis gave the following ratios: Ser 1.95; Gly 1.00.

EXAMPLE 3

N-Methyl-Tyrosyl-D-Seryl-Glycyl-N-Methyl-Phenylalanyl-D-Serine

Chloromethylated polystyrene resin is esterified with t-Boc-O-Benzyl-D-Serine according to the procedure of Gisin, Helv. Chim. Acta., 56, 1976 (1973), and the resulting polymeric ester is treated according to the procedure of Example 1 for incorporation of t-Boc-N-Me-Phe, t-Boc-Gly, t-Boc-O-Bzl-D-Ser, and t-Boc-N-Me-O-2,6-Cl-Bzl-Tyr. The resulting peptido resin is treated with HF as in Example 1, and the thus obtained title compound then purified and characterized according to the procedure of Example 2.

EXAMPLE 4

N-Methyl-Tyrosyl-D-Seryl-Glycyl-N-Methyl-Phenylalanyl-D-Serine-Ethylamide

Treatment of the peptido resin of Example 3 with ethylamine in a sealed flask for 10 hours followed by removal of excess ethylamine, extraction with dimethylformamide, filtration, and evaporation of the filtrate yields the title compound.

EXAMPLE 5

When N-Me-Tyr-D-Ser-Gly-N-Me-Phe-D-Ser-NH$_2$, acetate was tested in the rat-tail flick procedure of D'Amour and Smith (supra), the following results were obtained:

| Dose mg/kg. | Route | No. Showing Analgesia/No. Tested (Minutes) | | | | |
|---|---|---|---|---|---|---|
| | | 15 | 30 | 60 | 90 | 120 |
| 5.0 | i.v. | 4/4 | 3/3 | 3/3 | (3/6 dead) | |
| 1.0 | i.v. | 6/6 | 6/6 | 6/6 | | |
| 0.1 | i.v. | 3/6 | 5/6 | 5/6 | | |

| Dose | | No. Showing Analgesia/No. Tested (Minutes) | | | | |
|---|---|---|---|---|---|---|
| mg/kg. | Route | 15 | 30 | 60 | 90 | 120 |
| 0.5 | s.c. | | 2/6 | 2/6 | 1/6 | 1/6 |
| 1.0 | s.c. | | 6/6 | 6/6 | 6/6 | 5/6 |

What is claimed is:

1. A compound of the formula:

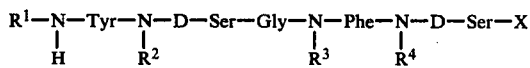

wherein $R^1$ is hydrogen, methyl, ethyl, propyl, 2-methyl-2-pentenyl, 2-methyl-1-pentenyl; cyclopropylmethyl, or cyclobutylmethyl; $R^2$, $R^3$, and $R^4$ are, independently, hydrogen or methyl; and X is $-NH_2$, $-NHC_nH_{2n+1}$ where n is 1, 2, 3, or 4, $-OR^5$, or $CH_2OR^5$, where $R^5$ is hydrogen or lower alkyl of from 1 to 4 carbon atoms; or a pharmaceutically acceptable salt thereof.

2. The compound of claim 1, N-Methyl-Tyrosyl-D-SerylGlycyl-N-Methyl-Phenylalanyl-D-Serinamide, or a pharmaceutically acceptable salt thereof.

3. The compound of claim 1, N-Methyl-Tyrosyl-D-SerylGlycyl-N-Methyl-Phenylalanyl-D-Serineethylamide, or a pharmaceutically acceptable salt thereof.

4. The compound of claim 1, N-Methyl-Tyrosyl-D-SerylGlycyl-N-Methyl-Phenylalanyl-D-Serine, or a pharmaceutically acceptable salt thereof.

5. t-Boc-N-Me-(O-2,6-Cl-Bzl)-Tyr-(O-Bzl)-D-Ser-Gly-N-Me-Phe-(O-Bzl)-D-Ser-$NH_2$.

* * * * *